United States Patent [19]
Hill, Jr. et al.

[11] Patent Number: 5,850,285
[45] Date of Patent: Dec. 15, 1998

[54] ADVANCED MISSILE APPROACH WARNING SYSTEM (AMAWS) AND STEALTH (LOW OBSERVABLES) DETECTION BASED ON EXPLOITATION OF QUANTUM EFFECTS

[75] Inventors: Ralph H. Hill, Jr.; James R. Keys, both of San Antonio, Tex.

[73] Assignee: Southwest Research Institute, San Antonio, Tex.

[21] Appl. No.: 868,701

[22] Filed: Jun. 4, 1997

Related U.S. Application Data

[60] Provisional application No. 60/022,075 Jul. 29, 1996.

[51] Int. Cl.$^6$ .......................... G01N 21/62; G01N 21/63
[52] U.S. Cl. .................................... 356/311; 356/318
[58] Field of Search ................... 356/311, 317, 356/318, 417

[56] References Cited

U.S. PATENT DOCUMENTS

| | | | |
|---|---|---|---|
| 3,653,016 | 3/1972 | Cormier | 340/228 |
| 3,665,440 | 5/1972 | McMenamin | 340/228.2 |
| 3,768,908 | 10/1973 | Zaromb . | |
| 3,848,129 | 11/1974 | Figler et al. | 250/339 |
| 4,270,613 | 6/1981 | Spector et al. | 169/61 |
| 4,362,388 | 12/1982 | Egan et al. | 356/341 |
| 4,517,458 | 5/1985 | Barringer | 250/253 |
| 4,572,667 | 2/1986 | Rogers | 356/317 |
| 4,765,244 | 8/1988 | Spector et al. | 102/213 |
| 4,802,762 | 2/1989 | Hill, Jr. | 356/318 |
| 4,849,620 | 7/1989 | Guerin et al. | 250/203 R |
| 4,866,283 | 9/1989 | Hill, Jr. | 250/461.2 |
| 5,093,574 | 3/1992 | Pratt et al. | 250/339 |
| 5,282,013 | 1/1994 | Gregoris | 356/4.07 |
| 5,300,780 | 4/1994 | Denney et al. | 250/342 |
| 5,373,358 | 12/1994 | Adachi | 357/301 |
| 5,384,589 | 1/1995 | Ulich et al. | 348/31 |
| 5,625,452 | 4/1997 | Hasson | 356/326 |
| 5,677,761 | 10/1997 | Hasson | 356/4.07 |

*Primary Examiner*—F. L. Evans
*Attorney, Agent, or Firm*—Jenkens & Gilchrist

[57] ABSTRACT

A method and apparatus based on the exploitation of quantum effects related to stimulated emission for detecting the presence of aircraft or missile exhaust plumes in the atmosphere. In the preferred embodiment, the present invention is directed toward detecting electromagnetic radiation due to the presence of chemical compounds existing in the exhaust plume which occur in areas of the spectrum not normally interrogated; that is, in the regions of 0.2–200 microns and 1 KHz–1000 GHz.

20 Claims, 3 Drawing Sheets

ADVANCED MISSILE APPROACH WARNING SYSTEM (AMAWS) AND STEALTH (LOW OBSERVABLES) DETECTION BASED ON EXPLOITATION OF QUANTUM EFFECTS

BACKGROUND OF THE INVENTION

1. Field of the Invention

The present invention relates generally to the field of missile and aircraft detection. More specifically, the present invention provides a method and apparatus for utilizing stimulated emission as a means of detecting the presence of missile or aircraft exhaust plumes in the atmosphere. This application claims the benefit of U.S. Provisional Application No. 60/022,075, filed on Jul. 29, 1996.

2. Background of the Invention

Targeted objects, particularly air-to-air (or surface-to-air) missiles, present an increasing threat to vehicles such as aircraft, tanks, armored personnel carriers and self-propelled guns. So far as vehicles are concerned, these are particularly threatened by the anti-tank guided missile, the shoulder-fired rocket, artillery and air deliverable guided and cluster munitions, as well as a variety of hollow-charge tipped weapons. Such incoming objects may be unguided, but are more usually manually wire guided, beam riding, and increasingly, fully-automatic, embodying fire and forget systems.

There are a number of possible solutions to the problem of damage and casualties due to the incoming object hitting its target. However, the preferred solution employs detection of the incoming object prior to impact. Such objects frequently emit a plume of very hot gases and/or flames which may be detected at a distance by infrared (IR) detectors, and at a much reduced distance, when the intensity of the plume radiation is greater than the solar background radiation, by ultraviolet (UV) sensors. A combination of such generic UV and IR sensors may also be used to detect the incoming objects. A number of such fire or explosion detection systems employing UV and IR detectors in combination are known. Examples of such systems are illustrated in the following U.S. Pat. Nos.: 3,665,440; 3,653,016; 4,270,613; and 4,765,244. Each of these inventions provides an alarm output when a combination of infrared and ultraviolet radiation is detected or when such radiation is detected in the absence of other radiation.

Another approach to the problem is to make use of infrared detection and pass-band filters to discriminate between missiles or aircraft and non-threatening objects such as a cloud or a flare. This solution is exemplified by U.S. Pat. Nos. 3,848,129, 4,849,620, and 5,093,574. Each of these inventions operates by observing spectral emissions from a given object and discriminating those emissions from others which may exist in the view field by looking for spectral absorption of chemical components known to exist in the exhaust, such as $CO_2$. A variation on this theme is exemplified by U.S. Pat. No. 5,300,780, which describes a multi-spectral signature analysis technique using several different frequency bands to assist in discriminating a missile launch (for example) from background radiation.

Each of the above methods for detection is based on generic detection of UV or IR radiation using broad band sensors or narrow band detection based on spontaneous emission (fluorescence) in the near IR (1–3 micron wavelength) of known chemical components which exist in the exhaust plume of a missile or aircraft. Each of the above systems also operates in a passive mode.

Other chemical component detection systems exist which operate in an active mode; using a laser or radar to irradiate the desired target, causing it to fluoresce. Examples of these systems are disclosed by U.S. Pat. No. 3,768,908, which makes use of fluorescence and Raman backscatter to detect the existence of air pollutants and U.S. Pat. No. 4,517,458, which irradiates the land or sea for detection of aerosols via fluorescence. Laser-induced fluorescence is also used to detect specific properties of materials or measure the characteristics of a substance. Examples of this are contained in U.S. Pat. No. 4,572,667, which discloses the use of laser-induced fluorescence to determine the pressure and density of air and U.S. Pat. Nos. 4,866,283 and 4,802,762, which use laser-induced fluorescence to determine physical characteristics of organic and polymeric materials.

Other systems use the Raman scattering effect to determine physical properties of various materials. Examples of these include U.S. Pat. No. 4,362,388, to detect the concentration of gas species remotely; U.S. Pat. No. 5,373,358, which makes use of a swept-spectrum Raman spectroscopic apparatus; and U.S. Pat. No. 5,384,589, which uses UV fluorescence and Raman scattering to probe spectrally-dependent optical properties of a scene.

SUMMARY OF THE INVENTION

Most of the prior art relies on atomic or molecular absorption for the detection of chemical compounds which are known to exist within the area being examined. Others make use of fluorescence (laser-induced or via Raman backscatter) to detect the presence of these compounds.

Another mechanism for detection which makes use of enhanced signal strength is stimulated emission. The primary advantage of using stimulated emission and/or superradiance to detect exhaust plumes is that the cooperative (coherent) effect of N radiating dipoles can be much higher than the incoherent effects. This is well understood in the operation of lasers, masers, and phased array antennas. Examples of stimulated emission which occur in nature are maser emissions from interstellar space (ref. "Masers in the Sky," *Scientific American,* February 1995, p. 68) and the 169-micron laser emission observed by NASA's Kuiper Airborne Observatory (ref. "Natural Laser Observed in Space," *Optics and Photonics News,* November 1995, p. 8).

In the present invention, prior knowledge of the combustion processes can be used to calculate which resonant transitions will exhibit stimulated emission. Narrow-band detectors can be tuned to those particular frequencies for enhanced detection capabilities. For example, most missile motors have nitrogen-containing fuels. During combustion, ammonia-like compounds will be produced in excited molecular states. As a specific example of the described process, ammonia microwave transitions near 25 GHz are a possible region of interest in missile plumes, as is the 10.6-micron transition in aircraft plumes originating from $CO_2$ excitation and radiation. Therefore, by utilizing the specific frequencies mentioned, two detectors, one on-resonance, and one off-resonance can be used to differentiate missile approaches. This is known as a "two-color scheme" where, for example, detection of a He—Ne 633-nanometer (nm) laser beam can be effected by a 633-nm filter used as the on-resonance detector and a 600-nm filter is used as the off-resonance or background detector. The difference in signal strength between these filters, or the ratio of their relative signal strengths, is used to provide detection of the 633-nm signal. More sophisticated schemes, such as three-color or four-color systems, can be used to further discriminate or detect a desired target in the presence of noise.

Finally, time domain differentiation can be used to detect the desired object. That is, the existence of radiation for a particular period of time may signal the presence of the desired target.

These concepts are not limited to missile detection, but can also be used for detection of "stealth" aircraft and the like. Obviously, the transition frequencies will be different. These concepts apply to active as well as passive systems.

It is an object of the present invention to provide a novel method of passively detecting aircraft or missile exhaust plumes using stimulated emission.

It is a related object of the present invention to provide a method for the detection of aircraft or missile exhaust plumes using stimulated emission which is brought into existence by the active irradiation of molecules present in the plume.

It is another object of the present invention to provide a system which is capable of detecting aircraft or missile exhaust plumes using stimulated emission.

It is yet another object of the present invention to provide a method for the detection of aircraft and missile plumes which relies on the process of stimulated emission and, as a result, is directed toward detection of frequencies not normally suggested by conventional IR or UV detection techniques.

A still further object of the present invention is to make use of stimulated emission as a means of detecting the excited molecular states present in the exhaust plumes of aircraft and missiles.

In satisfaction of these and related objectives, Applicant's present invention provides a novel method and system to detect the presence of aircraft and missile exhaust plumes in the atmosphere. Applicant's invention permits its practitioner to detect the presence of these plumes by directing a search in specific areas of the electromagnetic spectrum which are not usually addressed by conventional UV and IR detection methods.

DETAILED DESCRIPTION OF THE PREFERRED EMBODIMENT

Figure 1:
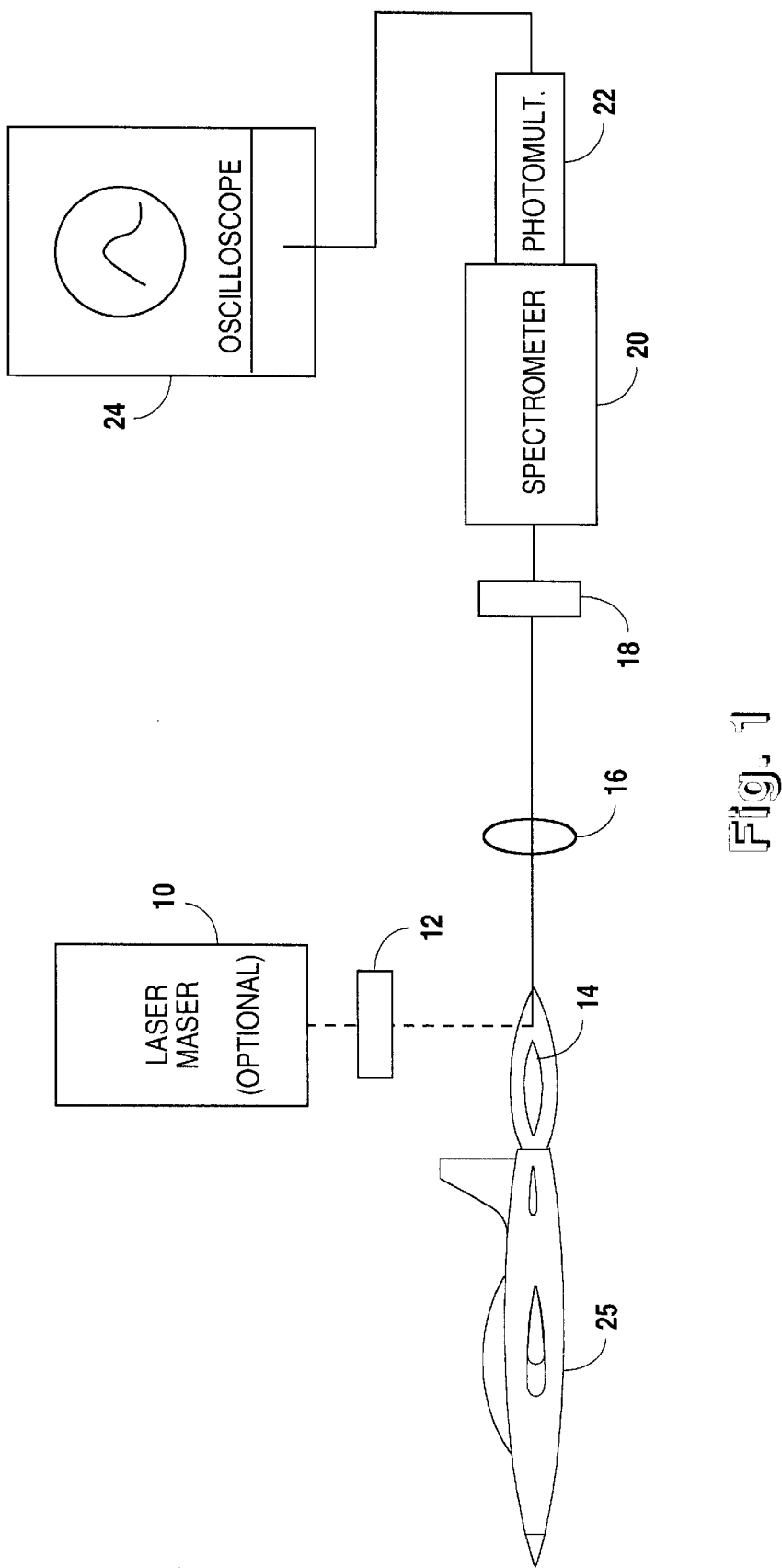
FIG. 1 is a schematic representation of the system configuration of the preferred embodiment used to measure luminescence of an exhaust plume as a function of time.

The phenomena which are principally responsible for the interaction of radiation with matter in every day life are absorption and reflection, or scattering. Less commonly encountered but still an important phenomena in nature is spontaneous emission (fluorescence). Light falling on matter is absorbed, leaving atoms or molecules in excited states which spontaneously emit radiation with a spread of frequency inversely proportional to the decay time. Laser-induced fluorescence occurs when a laser is used to excite the atoms and molecules, causing spontaneous emission.

It is stimulated emission which enables a medium to amplify incident radiation. When atomic or molecular decay times are sufficiently long and the radiation sufficiently intense, radiation may fall on excited atoms, resulting in stimulated emission rather than absorption. The LASER (an acronym for Light Amplification by Stimulated Emission of Radiation) and MASER (an acronym for Microwave Amplification by Stimulated Emission of Radiation) are commonly known examples of this amplification. (Note: The line strength ratios will change with stimulated emission effects.)

Stimulated emission usually requires a population inversion, i.e., more atoms or molecules in the excited state than in a lower state. It also depends on the quantum mechanical transition probabilities existing between these states. In a laser, mirrors are usually located so that a light (or microwave) beam can bounce back and forth so as to be amplified many times before transmission. If there are no mirrors, background-blackbody radiation or spontaneous emission from some of the atoms or molecules within the medium may also stimulate lasing action. This is normally an unwanted effect (causing significant problems in some chemical laser systems), since lasing action will occur in unwanted directions. However, this type of stimulated emission rarely occurs, and therefore is neglected in most calculations; for instance, it is not presently taken into account in most atmospheric absorption models (such as LOWTRAN, an atmospheric transmittance/radiance computer code) or in various simulation codes (such as SPIR-ITS: Spectral In-Band Radiometric Imaging of Targets and Scenes).

Certain applications, however, demand that stimulated emission be taken into account. Three specific examples are: (1) laser-induced fluorescence-experiments in atomic vapors; where background-blackbody stimulated emissions can lead to unwanted depletion of excited states during collision cross-section measurements; (2) Very-Low-Frequency (VLF) "whistler" waves in the atmosphere as amplified by interaction with the magnetosphere; and (3) infrared emissions which are significantly enhanced while viewing an aurorally excited atmosphere.

Stimulated emission occurs via processes in aircraft or missile exhaust plumes analogous to those which are present within a chemical laser. For example, a hydrogen fluoride laser is essentially a combuster with mirrors. A hydrogen-containing compound is burned in a fluorine-containing compound; the resulting population inversion of the hydrogen fluoride molecules can then be stimulated to lase. For combustion of hydrocarbon jet-fuel compounds, the reaction products are basically $CO_2$ and $H_2O$, with some of these molecules existing in excited states. When the $H_2O$, $CO_2$, or hydrocarbon molecules obtain a population inversion, the background-blackbody radiation (from the surroundings) can stimulate emission from these excited molecules. Since stimulated emission does not normally occur between states when one of the transition states is the ground state, and atmospheric absorption bands are such that the initial state is the ground state, this stimulated emission may be in a region of the spectrum where the atmosphere transmits well. In this case, such stimulated emission may be readily observed.

Another consideration which affects ease of observation is gain length—the distance over which stimulated emission occurs. This is analogous to the physical length of a laser cavity. For low-gain systems, the length is long (such as in an argon-ion laser), for high gain systems, the length is short (such as with a diode laser in a compact-disc player). For aircraft or missile applications, the plume size determines the gain length, so that when looking along the longitudinal axis of a plume, the amplified spontaneous emission (ASE)

will be highest. The longer the gain length, the greater the intensity of the ASE, since: $I/I_o=e^{GL}$, where $I/I_o$=ratio of exciting intensity to the initial intensity of the background blackbody radiation and GL=gain length product (i.e. gain per unit length×length).

Stimulated emission may also occur via energy transfer between chemical species through intermediaries such as molecular nitrogen existing in metastable states (active nitrogen). Nitrogen has many long-lived metastable states, which are the source of various effects in nitrogen afterglows, auroras, and other chemiluminescent effects. For instance, these metastable states may transfer energy to $H_2O$ molecules (through collisions) which subsequently emit over a broad wavelength range. One example of such energy transfer is used in the commercially available Transverse Electric-discharge Atmospheric (TEA) $CO_2$ laser, where molecular nitrogen is used to optimize the energy transfer to $CO_2$. Another example of this energy transfer makes use of an extremely long-lived metastable state for oxygen, the so-called "$O_2$ singler-delta" state, which is used as the pump reaction in the oxygen-iodine chemical-transfer laser developed by the Air Force Phillips Laboratory.

Figure 2:
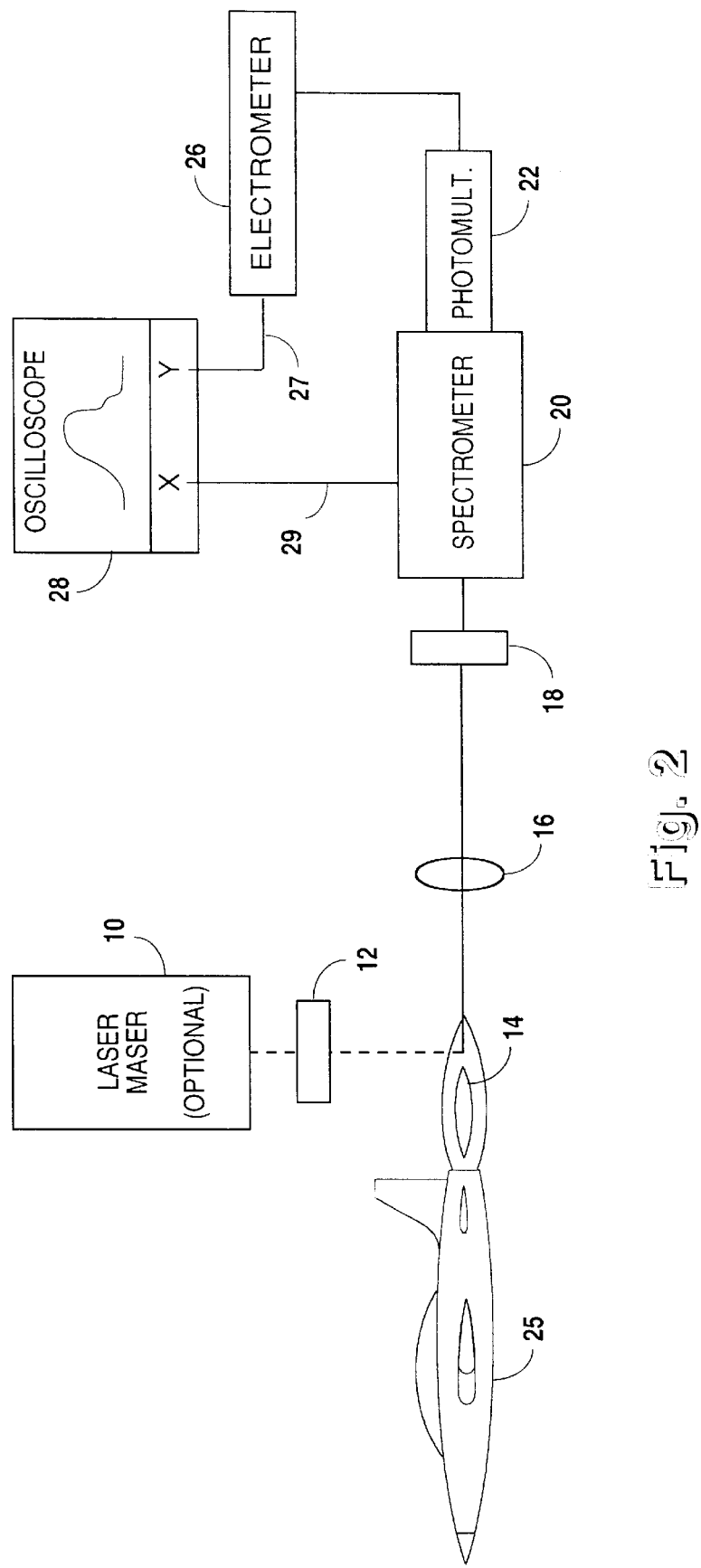
FIG. 2 is a schematic representation of the system configured for measurement of the luminescence of an exhaust plume as a function of wavelength.

The preferred embodiment of the invention for detection of quantum effects (including fluorescence and stimulated emission) in aircraft or missile exhaust plumes is shown generally in FIGS. 1 and 2. As discussed above, the invention is based on the existence of molecular species which have been excited by transfer of energy from "active nitrogen" (molecular nitrogen existing in metastable states), or other metastable molecules. These other species may include $CO_2$, CO, $NO_2$, $H_2O$, and other atomic or ionic species, such as oxygen. Since the invention for detecting stimulated emission is intended to be used on a wide variety of combustible matter used in both aircraft and missiles, it is necessary to make an initial determination of characteristics for a particular fuel. The apparatus depicted in FIGS. 1 and 2 can be used to establish a reference spectral response for any particular combustible matter. Once the reference characteristics of the combustible matter have been determined, these characteristics can be stored and correlated with subsequent measurements of unknown specimens. As an alternative, a chemical analysis can be conducted to determine the species present in a particular exhaust plume, which in turn will provide a means of calculating the expected transition frequencies.

Referring now to FIG. 1, and considering a purely passive detection system, an aircraft or missile (25) is used to produce a specimen exhaust plume (14). As the atoms or molecules present in the specimen exhaust plume (14) radiate by means of stimulated emission, the radiated electromagnetic emissions pass through a lens (16), a filter (18), and into a spectrometer (20). The spectrometer (20) disperses the radiation which is then sensed by a detector (22) and amplified to provide input for a suitable display device, such as an oscilloscope (24). (Note: this description is for visible or infrared electromagnetic radiation; for radio frequency radiation, the elements would be replaced with corresponding antennas, etc.)

Referring now to FIG. 2, it can be seen how the intensity of radiation can be measured as a function of wavelength. Many of the same structural elements are present as were shown in FIG. 1. In this case, however, the output of the photomultiplier is fed to an electrometer (26) which provides an amplitude signal (27) for stimulated emission. Display can be effected by directing the amplitude signal (27) into a chart recorder (28). The wavelength information for stimulated emission is directed to the chart recorder (28) using a wavelength output (29) from the spectrometer (20).

These same measurements can be made using a laser or maser (10) to actively induce stimulated emission radiation in the specimen exhaust plume (14). (Note: Angle of laser beam will be varied.)

Referring to FIGS. 1 and 2, radiation from the laser or maser (10) can be passed through a shutter (12) to impinge on and irradiate molecules present in the specimen exhaust plume (14). The signal from the laser or maser (10) provides additional energy to produce stimulated emission within the specimen exhaust plume (14).

Figure 3:
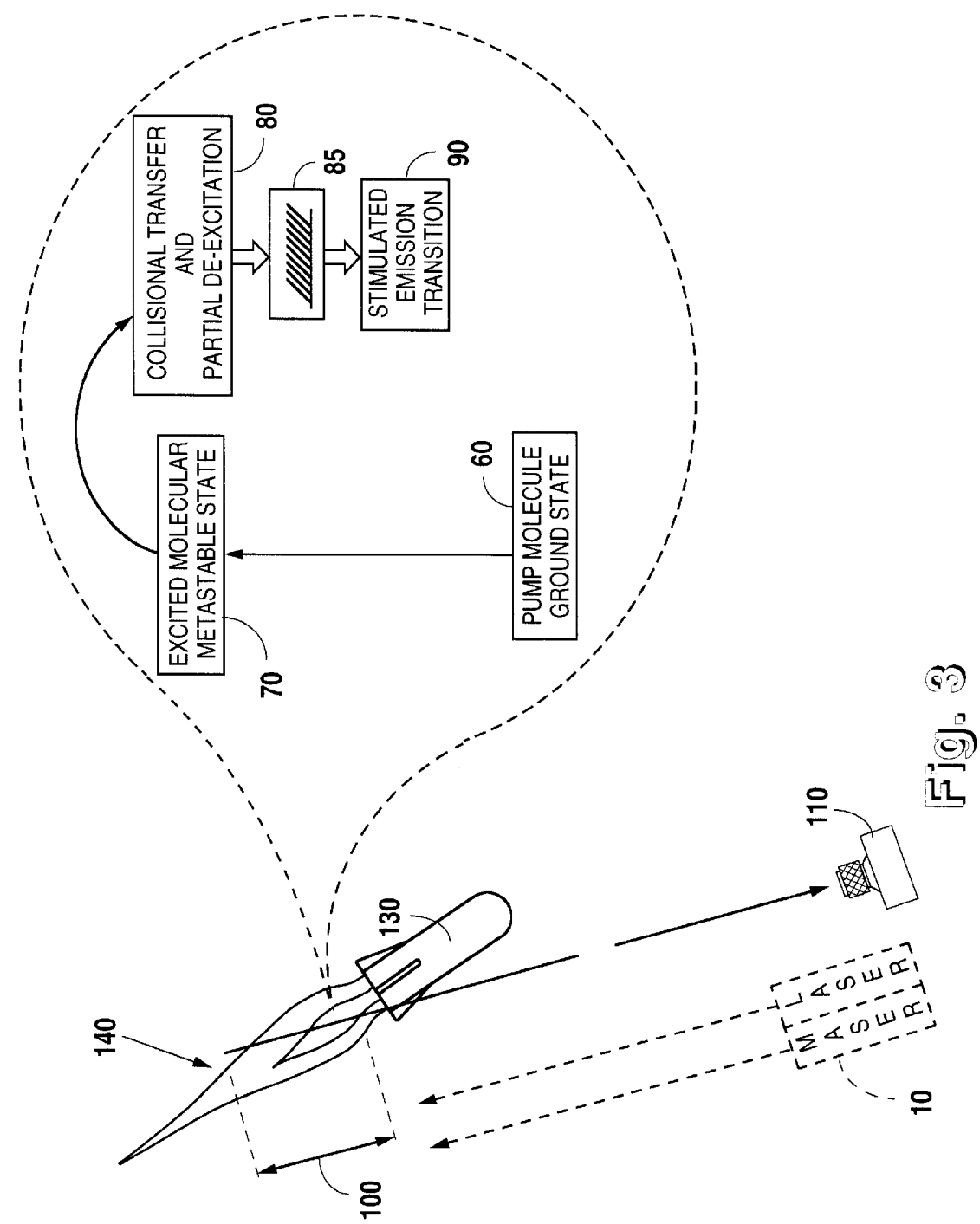
FIG. 3 is a schematic representation of the preferred embodiment for a system configuration used to detect stimulated emission.

Referring generally to FIG. 3, the combustion of jet fuel or solid rocket fuel places some species (especially from the included impurities) which are initially in the ground state (60) into excited states, resulting in similar effects. This occurs as follows: metastable nitrogen molecules (70), i.e., active nitrogen, are created by collisions with hot combustion gases, which end up behind the aircraft in the exhaust plume (140) of the aircraft or missile (130). Because these molecules are metastable, they remain in excited states for relatively long periods of time. In close proximity to the active nitrogen are transfer molecules that have been formed in the combustion process. Nitrogen collisionally transfers energy (80) to the transfer molecules along the length of the exhaust plume (140) behind the aircraft (130). In that region, there are small intensities of all wavelengths due to the background-blackbody radiation as well as resonant radiation due to spontaneous emission from the transfer molecules themselves. This radiation is the initial radiation (85) that subsequently stimulates the excited molecules to radiate (90), preferentially along the directions of long gain length (100).

In the case of stimulated emission, the system may again act in either a passive or active fashion. A narrow band sensor (110) may be used in a purely passive mode to detect stimulated emission from the exhaust plume (140). The narrow band sensor (110) is tuned to a particular frequency or set of frequencies which have previously been determined by predictive calculation or sampling of specimen exhaust plumes, as described above. In addition, a laser or maser (10) can be aimed to impinge upon the field of view covered by narrow band sensor (110) to include exhaust plume (140), when stimulated emission by active irradiation is desired. Of course, to stimulate (and detect) emission in the RF spectrum, appropriate antennas, power amplifiers, and oscillators can be used.

Tactical missile exhaust parameters are more complicated to determine than that of aircraft. There are separate phases for eject, boost, sustain, burn-out, and post-burn-out. Detection of ASE may be more effective in some phases, such as the boost phase, than in others. Also, patterns of ASE, combined with the gain length product, can provide a basis for early determination of the probable source of the ASE—whether a threat is presented, or whether the source is merely a flare, friend, or countermeasure.

The novelty of the present invention does not reside in detection of radiation in the normally expected regions, such as 3–15 μm. What is novel about this invention is the use of quantum effects, such as stimulated emission to predict and acquire samples of radiation in those areas of the electromagnetic spectrum which have heretofore been overlooked, at least in the area of aircraft or missile detection. Specifically, radiation in the regions of 0.2–200 microns, or the RF wavelengths depicted in Table 1, is anticipated for these techniques. Such wavelengths may provide for windows of detection which transmit well through the atmosphere, unlike some of the emissions observed using conventional UV and IR detection methods, especially those using wide band detectors. Additionally, the phenomena of stimulated emission provides for a greatly increased signal strength. This means that, for a given frequency, the signal resulting from stimulated emission will be inherently easier to detect than that resulting from mere spontaneous emission (fluorescence). Maximizing the detected ASE signal also provides a way to track the source in space.

TABLE I

Possible Stimulated Emission Transitions of Interest

| Species | Frequency |
|---------|-----------|
| $NH_3$  | 18.5 GHz  |
|         | 19.7 GHz  |
|         | 23.870 GHz|
| OH      | 1.665 GHz |
|         | 1.667 GHz |
|         | 1.612 GHz |
|         | 1.720 GHz |
| $H_2O$  | 22 GHz    |
| $CO_2$  | 10.6 μm   |

Although the invention has been described with reference to specific embodiments, this description is not meant to be construed in a limited sense. For example, these concepts also apply to other regions of the electromagnetic spectrum, such as radio, microwave, and millimeter waves. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

We claim:

1. A method for detecting the presence of aircraft or missile plumes in the atmosphere using stimulated emission, comprising the steps of:

obtaining a chemical analysis of the chemical composition of a first exhaust plume;

first detecting stimulated emission produced by said first exhaust plume;

first producing a first data signal proportionate to said stimulated emission produced by said first exhaust plume;

recording said first data signal;

second detecting stimulated emission in the atmosphere;

second producing a second data signal proportionate to said stimulated emission detected in said atmosphere; and comparing said second data signal to said recorded first data signal to obtain an indication of the presence of a second exhaust plume.

2. The method according to claim 1, further including, prior to said first detecting step, the step of irradiating said first exhaust plume with coherent radiation and prior to said second detecting step, the step of irradiating said atmosphere with coherent radiation.

3. The method according to claim 1, wherein said comparing step is effected using an optical multi-channel analyzer.

4. The method according to claim 2, wherein said comparing step is effected using an optical multi-channel analyzer.

5. The method according to claim 1, wherein said first producing step and said second producing step includes the production of a data signal responsive to stimulated emission in the range of 0.2–200 microns.

6. The method according to claim 2, wherein said first producing step and said second producing step includes the production of a data signal responsive to stimulated emission radiation in the range of 0.2–200 microns.

7. The method according to claim 1, wherein said first producing step and said second producing step includes the production of a data signal responsive to stimulated emission in the range of 1 KHz–1000 GHz.

8. The method according to claim 2, wherein said first producing step and said second producing step includes the production of a data signal responsive to stimulated emission radiation in the range of 1 KHz–1000 GHz.

9. The method according to claim 1, further including, subsequent to said comparing step, the step of monitoring the spatial location of said second exhaust plume in said atmosphere relative to the location of the detecting apparatus used to effect said second detecting step by maximizing the amplitude of said second data signal.

10. The method according to claim 1, further including, subsequent to said comparing step, the step of determining the spatial location of the long axis of said second exhaust plume in said atmosphere relative to the location of the detecting apparatus used to effect said second detecting step by maximizing the amplitude of said second data signal.

11. The method according to claim 1, further including, subsequent to said comparing step, the step of determining the type of object which is the probable source of said second exhaust plume by comparing said second data signal and said indication of the presence of a second exhaust plume to previously obtained experimental exhaust plume data.

12. A system for detecting the presence of aircraft or missile exhaust plumes in the atmosphere, comprising:

a reference signal memory containing electromagnetic emission signal data predicted by calculations based on the presence of known chemical compounds and combustion processes which exist in a multiplicity of reference sample exhaust plumes, said electromagnetic emission signal data representing the stimulated emission signatures of said reference sample exhaust plumes;

a narrow band electromagnetic sensor for detecting stimulated emission in said atmosphere and providing a signal responsive thereto;

an optical multi-channel analyzer, said optical multi-channel analyzer effecting a comparison between said electromagnetic emission signal data and said signal provided by said narrow band electromagnetic sensor; and a display unit to display the result of said comparison.

13. The system of claim 12, wherein said system includes a LASER or MASER for inducing stimulated emission in said reference sample exhaust plumes and said atmosphere.

14. The system of claim 12, wherein said narrow band electromagnetic sensor is capable of responding to stimulated emission in the range of 0.2–200 microns.

15. The system of claim 12, wherein said narrow band electromagnetic sensor is capable of responding to stimulated emission in the range of 1 KHz–1000 GHz.

16. A system for detecting the presence of aircraft or missile exhaust plumes in the atmosphere, comprising:

a reference signal memory containing electromagnetic emission signal data determined by testing for the presence of stimulated emission in a multiplicity of reference sample exhaust plumes, said electromagnetic emission signal data representing the stimulated emission signatures of said reference sample exhaust plumes;

a narrow band electromagnetic sensor for detecting stimulated emission in said atmosphere and providing a signal responsive thereto;

an optical multi-channel analyzer, said optical multi-channel analyzer effecting a comparison between said electromagnetic emission signal data contained in said reference signal memory and said signal provided by said narrow band electromagnetic sensor; and a display unit to display the results of said comparison.

17. The system of claim 16, wherein said system includes a LASER or MASER for inducing stimulated emission in said reference sample exhaust plumes and said atmosphere.

18. The system of claim 16, wherein said narrow band electromagnetic sensor is capable of responding to stimulated emission in the range of 0.2–200 microns.

19. The system of claim 16, wherein said narrow band electromagnetic sensor is capable of responding to stimulated emission in the range of 1 KHz–1000 GHz.

20. A system for detecting the presence of aircraft or missile exhaust plumes in the atmosphere, comprising:

a reference signal memory containing electromagnetic emission signal data predicted by calculations based on the presence of known chemical compounds and combustion processes which exist in a multiplicity of reference sample exhaust plumes, said electromagnetic emission signal data representing the stimulated emission signatures of said reference sample exhaust plumes;

a narrow band electromagnetic sensor for detecting stimulated emission in said atmosphere and providing a signal responsive thereto;

a signal comparator, said signal comparator effecting a comparison between said electromagnetic emission signal data and said signal provided by said narrow band electromagnetic sensor; and a display unit to display the result of said comparison.

\* \* \* \* \*